(12) United States Patent
Van Vugt et al.

(10) Patent No.: US 9,993,195 B2
(45) Date of Patent: Jun. 12, 2018

(54) PERSONALIZED SLEEP DISTURBANCE MONITORING APPARATUS AND METHOD WITH CORRELATION OF SLEEP SIGNALS AND AMBIANCE DISTURBANCE SIGNAL

(75) Inventors: Henriette Christine Van Vugt, Utrecht (NL); Roy Joan Eli Marie Raymann, Waaire (NL); Vincentius Paulus Buil, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1003 days.

(21) Appl. No.: 13/885,179

(22) PCT Filed: Nov. 28, 2011

(86) PCT No.: PCT/IB2011/055344
§ 371 (c)(1),
(2), (4) Date: Aug. 29, 2013

(87) PCT Pub. No.: WO2012/073183
PCT Pub. Date: Jun. 7, 2012

(65) Prior Publication Data
US 2013/0338446 A1    Dec. 19, 2013

(30) Foreign Application Priority Data
Dec. 3, 2010   (EP) .................................... 10193682

(51) Int. Cl.
*A61B 5/00* (2006.01)
*A61M 21/02* (2006.01)
(Continued)

(52) U.S. Cl.
CPC ............ *A61B 5/4815* (2013.01); *A61B 5/486* (2013.01); *A61B 5/4806* (2013.01);
(Continued)

(58) Field of Classification Search
None
See application file for complete search history.

(56) References Cited

U.S. PATENT DOCUMENTS

| 5,434,716 A | 7/1995 | Sugiyama et al. |
| 6,888,779 B2 * | 5/2005 | Mollicone ............. A61M 21/00 368/10 |

(Continued)

FOREIGN PATENT DOCUMENTS

| EP | 2278507 A2 | 1/2011 |
| WO | 2005066868 A2 | 7/2005 |
| WO | 2009108228 A1 | 9/2009 |

OTHER PUBLICATIONS

Iber et al: "The AASM Manual for the Scoring of Sleep and Associated Events: Rules, pp. 3Terminology and Technical Specifications", American Academy of Sleep Medicine, 2007, pp. 3-57.
(Continued)

*Primary Examiner* — Serkan Akar

(57) ABSTRACT

The invention relates to a sleep disturbance monitoring apparatus (1) for monitoring a sleep disturbance of a person. An ambience disturbance profile, which describes which levels and/or changes of an ambient signal, which is, for example, a temperature signal or a noise signal, are related to disturbed sleep, is amended depending on a correlation between the ambience signal and a sleep signal which is indicative of the quality of the sleep of the person. After the ambience disturbance profile has been amended, an environmental disturbance factor, which disturbs the sleep, is determined based on a comparison of an actual ambient signal with the amended ambience disturbance profile, wherein information regarding the determined environmental disturbance factor is output to the person on an output unit. This allows providing personalized information regarding environmental sleep disturbance factors, i.e. the information considers the individual susceptibility of a person for environmental disturbances during sleep.

11 Claims, 5 Drawing Sheets

(51) Int. Cl.
    *A61B 5/0476* (2006.01)
    *A61B 5/11* (2006.01)
    *A61M 21/00* (2006.01)

(52) U.S. Cl.
    CPC ............ *A61B 5/4812* (2013.01); *A61B 5/681* (2013.01); *A61B 5/6803* (2013.01); *A61B 5/6814* (2013.01); *A61B 5/72* (2013.01); *A61M 21/02* (2013.01); *A61B 5/0476* (2013.01); *A61B 5/11* (2013.01); *A61B 2560/0242* (2013.01); *A61M 2021/0027* (2013.01); *A61M 2021/0044* (2013.01); *A61M 2021/0066* (2013.01); *A61M 2205/3306* (2013.01); *A61M 2205/3375* (2013.01); *A61M 2205/3561* (2013.01); *A61M 2205/3592* (2013.01); *A61M 2230/10* (2013.01)

(56) References Cited

U.S. PATENT DOCUMENTS

| | | | |
|---|---|---|---|
| 2005/0177051 A1* | 8/2005 | Almen | A61B 5/02405 600/509 |
| 2007/0270706 A1 | 11/2007 | Merilainen et al. | |
| 2009/0121826 A1 | 5/2009 | Song et al. | |
| 2009/0264715 A1 | 10/2009 | Auphan | |
| 2010/0087701 A1* | 4/2010 | Berka | A61M 21/02 600/27 |
| 2010/0099954 A1 | 4/2010 | Dickinson et al. | |
| 2010/0152543 A1* | 6/2010 | Heneghan | G06F 19/3418 600/300 |

OTHER PUBLICATIONS

Rechtschaffen et al: "A Manual of Standardized Terminology, Techniques and Scoring System for Sleep Stages of Human Subjects"; U.S. Department of Health, Education and Welfare Public Health Service, 1968, 57 Page Document.

Berglund et al: "Guidelines for Community Noise"; World Health Organization, 1995.

Navara et al, "The Dark Side of Light at Night: Physiological, Epidemiological, and Ecological Consequences", J. Pineal Res, vol. 43, 2007, pp. 215-224.

"Blinded by the Light?", Downloaded From www.britastro.org/dark-skies on Feb. 14, 2017, 2009, pp. 1-40.

"Light Pollution", From Wikipedia Dowloaded on Feb. 14, 2017, 26 Pages.

Raymann et al, "Skin Deep: Enhanced Sleep Depth by Cutaneous Temperature Manipulation", Brain, vol. 131, 2008, pp. 500-513.

* cited by examiner

PERSONALIZED SLEEP DISTURBANCE MONITORING APPARATUS AND METHOD WITH CORRELATION OF SLEEP SIGNALS AND AMBIANCE DISTURBANCE SIGNAL

FIELD OF THE INVENTION

The invention relates to a sleep disturbance monitoring apparatus, a sleep disturbance monitoring method and a sleep disturbance monitoring computer program for monitoring the sleep disturbance of a person.

BACKGROUND OF THE INVENTION

The Zeo sleep monitor from the company Zeo, Inc. monitors sleep quality over time while a person is sleeping. After the person has woken up, the monitored sleep quality is shown on a display to the person. Since only the sleep quality is shown to the person, the person does not know why his sleep had the displayed quality. In particular, the person does not know which actions have to be taken, in order to improve his or her sleep quality, and, thus, based on the information provided by the Zeo sleep monitor it is very difficult to improve the sleep quality.

SUMMARY OF THE INVENTION

It is regarded as being an object of the invention to provide a sleep disturbance monitoring apparatus, a sleep disturbance monitoring method and a sleep disturbance monitoring computer program for monitoring the sleep disturbance of a person, which allow improving the sleep of the person.

In a first aspect of the present invention a sleep disturbance monitoring apparatus for monitoring a sleep disturbance of a person is presented, wherein the sleep disturbance monitoring apparatus comprises:
 an ambient sensor for generating an ambient signal, the ambient signal being indicative of a property of the environment of the person,
 an ambience disturbance profile providing unit for providing an ambience disturbance profile, the ambience disturbance profile describing which levels and/or changes of an ambient signal are related to disturbed sleep,
 a sleep sensor for generating a sleep signal over time, while the person is sleeping, the sleep signal being indicative of the quality of the sleep of the person over time,
 a correlation unit for correlating the ambient signal and the sleep signal,
 an ambience disturbance profile amending unit for amending the ambience disturbance profile depending on the correlation,
 an environmental disturbance determination unit for determining an environmental disturbance factor, which disturbs the sleep, based on a comparison of a generated ambient signal with the ambience disturbance profile,
 an output unit for outputting information regarding the determined environmental disturbance factor to the person.

Since the environmental disturbance determination unit determines an environmental disturbance factor like a too low or too high room temperature, a too loud noise level, a too brightlight intensity to which the person is exposed which disturbs the sleep, based on a comparison of the generated ambient signal with the amended and, thus, personalized ambience disturbance profile and since the output unit outputs information based on the determined environmental disturbance factor to the person, the person can take countermeasures for reducing, or eliminating, the determined environmental disturbance factor, in order to improve the quality of the sleep of the person. For example, it can be shown on a display to the person that an inappropriate room temperature, a too loud noise level and/or a too bright light intensity have disturbed the sleep, whereupon the person can modify the room temperature, reduce the noise level and/or reduce the light intensity, respectively, in order to improve the quality of the next sleep of the person.

The ambient sensor can be adapted for generating an ambient signal over time. For example, the ambient signal can be measured during the complete sleep time of the person.

The environmental disturbance factor is preferentially a property of the environment of the person, which has disturbed the sleep of the person. This property of the environment of the person is, for example, inter alia, the room temperature, the light intensity, the ambient noise, the humidity.

The sleep disturbance monitoring apparatus can comprise one or several of the ambient sensors. In particular, the sleep disturbance monitoring apparatus can comprise one or several of following ambient sensors: an audio sensor such as a microphone; a light sensor such as a white light or color spectrum light intensity sensor; a temperature sensor for measuring ambient temperature and/or skin temperature; an air quality sensor such as oxygen, nitrogen, humidity, scent sensors; a bed/chair movement sensor if the person is located on a bed or a chair, for example, in an aircraft, a bus, a car, a boat or a train. The ambient signal can be any signal being indicative of properties of the environment of the person including the temperature of the environment directly at the skin of the person, i.e. including the skin temperature.

The output unit can be adapted to output, inter alia, optical information, acoustical information. For example, the output unit can comprise a display and/or a loudspeaker. The output information is preferentially indicative of the one or several environmental disturbance factors determined by the environmental disturbance determination unit. For example, if the room or skin temperature has been determined as being an environmental disturbance factor, this can be shown on a display.

The ambience disturbance profile can comprise ranges of levels and/or of changes of environmental properties, wherein it is likely that the sleep is disturbed, if the level and/or change of the ambient signal is within these ranges. These ranges can be predefined ranges, which are, for example, known from literature or a questionnaire.

For instance, the ranges of the ambience disturbance profile can be predefined using published guidelines, in particular, published guidelines of the World Health Organization. For example, if the ambient signal is a noise signal, the continuous noise level should not exceed 30 dB, wherein the non-continuous noise should not exceed 45 dB as disclosed in the Guidelines for Community Noise, by Berglund B. et al., World Health Organization, 1999. Thus, in this example ambient signal ranges can be defined by a continuous noise level being larger than 30 dB and a non-continuous noise being larger than 45 dB. If an ambient sensor measures the room temperature, a temperature range being optimal for sleep can be regarded as being between 18° and 20° Celsius. In this case, an ambient signal level range could be defined by temperatures outside of the temperature range of 18° to 20° Celsius. If an ambient sensor measures the light intensity as ambient signal, an ambient signal level range can be defined as comprising intensities larger than 10 lux, because a light intensity being smaller than 10 lux is considered to not disturb the sleep.

The sleep signal can be a movement signal which can be determined by using, inter alia, three-dimensional accelerometry, an infrared camera, and/or sound analysis. The sleep signal can also be an electroencephalography (EEG) or polysomnography (PSG) recording. The sleep signal can also be a signal representing the sleep depth or sleep stage over time, wherein the sleep depth or sleep stage is determined based on, for example, detected movements of the person, EEG or PSG recordings. Also other means can be used to quantify the sleep depth or sleep stage for generating a sleep signal over time. Different sleep depths or sleep stages, can be discriminated by defining the sleep quality as wake, light sleep, deep sleep and rapid eye movement (REM).

The correlation unit can be adapted to determine whether a change and/or level of the ambient signal corresponds to a change in the sleep signal. The correlation unit, which can also be regarded as a reasoning engine, can therefore determine whether ambient changes and/or levels can be seen as an arousal in the sleep signal, in particular, in sleep depth data.

The ambience disturbance profile amending unit can be adapted to use data reasoning techniques such as neural networks to amend the ambience disturbance profile.

The environmental disturbance determination unit is adapted to determine the environmental disturbance factor based on a comparison of the generated ambient signal with the ambience disturbance profile. For example, if the level and/or a change of the ambient signal is within a range defined by the ambience disturbance profile, the environmental factor, to which the ambient signal relates, can be determined as being the environmental disturbance factor. For instance, if the ambient signal is a temperature signal and the level of the temperature signal is within a range defined by the ambience disturbance profile, the temperature can be determined as an environmental disturbance factor and this environmental disturbance factor can be output by the output unit.

It is preferred that the sleep disturbance monitoring apparatus further comprises an advice generating unit for generating advice for improving the sleep quality, wherein the advice generating unit is adapted to generate the advice depending on the determined environmental disturbance factor and wherein the output unit is adapted to output the advice to the user. For example, if the room temperature has been determined as being an environmental disturbance factor, an advice can be generated, which recommends to increase or decrease the room temperature. In general, the advice generating unit is preferentially adapted to generate advice recommending to decrease or increase the determined environmental disturbance factor, for example, to increase or decrease the room temperature, to decrease the noise level, to decrease the light intensity.

The sleep disturbance monitoring apparatus can comprise a sleep signal calculation unit for providing a calculated sleep signal over time from the ambience disturbance profile and the ambient signal. The sleep signal calculation unit can provide a calculated sleep signal over time from the ambience disturbance profile and the generated ambient signal, without needing the sleep sensor for generating the sleep signal. Thus, for example, in a training phase the sleep sensor and the ambient sensor are used for generating a sleep signal and an ambient signal for amending the ambience disturbance profile, wherein after the training phase and after the ambience disturbance profile has been amended, a calculated sleep signal over time, which is indicative of the quality of the sleep of the person over time, can be calculated from the ambience disturbance profile and the ambient signal, which is generated during the actual sleep of the person, without needing to measure an actual sleep signal by the sleep sensor while the person is sleeping. The sleep signal is, for example, a hypnogram.

It is further preferred that the sleep disturbance monitoring apparatus comprises an expected sleep quality determination unit for determining an expected sleep quality from the ambient signal and the ambience disturbance profile. The expected sleep quality determination unit gives a prognosis on expected sleep quality by sampling the properties of the environment like the noise, light, and temperature characteristics before going to sleep by using the one or several ambient sensors and by determining the expected sleep quality from the measured one or several ambient signals and the ambience disturbance profile. The ambient signal, which is used for determining the expected sleep quality, can be an ambient signal which has been measured during one or several earlier sleeping times of the person, for example, during one or several earlier nights. It is also possible that the ambient signal, which is used for determining the expected sleep quality, is measured directly before the person goes to sleep, wherein this ambient signal is used for determining the expected sleep quality. For example, if several ambient sensors measured several ambient signals related to different environmental properties like temperature, noise, and light intensity and if the level and/or the change of the ambient signals is not within the ranges defined by the ambience disturbance profile, the expected sleep quality can be determined as being a good sleep quality.

It is also preferred that the sleep disturbance monitoring apparatus comprises a disturbed period determination unit for determining a disturbed period during which the environment potentially disturbed the sleep, wherein the disturbed period determination unit is adapted to determine the disturbed period depending on the ambient signal and the ambience disturbance profile. In particular, if a level and/or a change of the ambient signal is within ranges defined by the ambient disturbance profile, the period, i.e. the time period, in which the level and/or change of the ambient signal was within a range defined by the ambience disturbance profile, is determined as being a disturbed period. The sleep disturbance monitoring apparatus can, for example, count or sum the events or time spent in an environmental situation that is considered as being not optimal for sleep. The disturbed period determination unit can be adapted to determine several disturbed periods, during which the person is disturbed while sleeping. The sum of these disturbed periods can be related to the total sleep time for determining a sum score that indicates the total amount of sleep disturbance in the sleep environment. For example, this sum score can be provided as the ratio of the sum of the disturbed periods to the complete sleeping time in percent. If several properties of the environment have been measured by using several ambient sensors, for example, if the noise, the temperature, the light intensity and/or the humidity have been measured as the several properties, for each single property a sub score can be calculated, wherein the sub score indicates the part of the sum of the disturbed periods or of the complete sleeping time, which has been disturbed by the respective property. Information representing the one or several determined disturbed periods, the sum score and/or the sub score can be shown on the display.

Information regarding the correlation of the ambient signal and the sleep signal can be shown on a display of the output unit. Since not only a sleep signal is generated over time, but also an ambient signal being indicative of properties of the environment of the person, and since the ambient signal and the sleep signal are correlated, it can be determined which change and/or level of the ambient signal has caused which change in the sleep signal. Thus, changes and/or levels of properties of the environment of the person, which have caused a change in the sleep signal and which may therefore have disturbed the sleep, can be identified, even if these changes and/or levels of properties of the environment of the person have not led to a conscious or unconscious wake up of the person. The effect of the identified environmental property changes and/or levels on the sleep of the person can be reduced, in order to improve the quality of the sleep of the person.

It is further preferred that the correlation unit is adapted to determine a degree of disturbance being indicative of an amount of the change in the sleep signal caused by a change and/or level of the ambient signal. The correlation unit can therefore give a kind of rating on how disturbing an ambient change and/or level was to the sleep signal, in particular, to the sleep depth or sleep stage. For example, the correlation unit can be adapted to classify the change and/or level of the ambient signal as little, medium, or very disturbing for the sleep.

If the output unit comprises a display, the display can show graphs and/or text to the person, in order to inform the person about the correlation between the ambient signal and the sleep signal. In particular, the display can be adapted to indicate which changes in the properties of the environment, i.e. which changes in the ambient signal, have caused which changes in sleep depth or sleep stage. The display can also be adapted to show other information like the calculated sleep signal, information describing the expected sleep quality, and/or the determined advice.

It is further preferred that the sleep disturbance monitoring apparatus comprises:
 a sleep depth transition determination unit for determining sleep depth transitions over time based on the sleep signal, and
 a sleep transition period determination unit for determining a sleep transition period during which the sleep depth changes over time based on the determined sleep depth transitions. Sleep transition periods can be classified depending on at least the occurrence of sleep depth transitions. In particular, the sleep transition periods can be classified depending on, for example, the detection of a transition in sleep depth, the direction of the transition, i.e. deeper or more shallow sleep, the amount of consecutive transitions, and/or the absolute sleep depth. In an embodiment, the sleep depth transition determination unit is adapted to determine sleep depth transitions from a deeper sleep to a shallower sleep, wherein the depth of the sleep is determined based on the sleep signal and wherein the sleep transition period determination unit is adapted to determine a sleep transition period during which the sleep depth changes from a deeper sleep to a shallower sleep based on the determined sleep depth transitions. Moreover, a disturbed sleep period determination unit can be provided, wherein the disturbed sleep period determination unit is adapted to determine a disturbed sleep period depending on the determined sleep transition period and the ambient signal. A disturbed sleep period defines a period during which the sleep was disturbed by an environmental disturbance factor like noise, light, and/or temperature. Thus, the disturbed sleep period determination unit can be adapted to count or sum the events or times spent in an environmental situation within a time frame determined by the sleep transition period determination unit that coincide with sleep changes towards a lighter sleep depth. The sleep transition periods can be correlated with the ambient signal, in order to determine which sleep transition period coincides with which change and/or level of the properties of the environment. For example, if during a sleep transition period, during which the sleep depth changes from a deeper sleep to a shallower sleep, noise above a predefined threshold has been determined as environmental disturbance factor, this sleep transition period can be determined as being a disturbed sleep period which is caused by noise. In particular, it can be determined whether recorded noise coincides with a shift to lighter sleep or even wake. The sleep transition periods can therefore be classified in accordance with correlated changes and/or levels of the properties of the environment, in order to determine disturbed sleep periods. During a sleep of the person, several disturbed sleep periods can be determined which are related to one or several properties of the environment. The sum of these disturbed sleep periods can be regarded as a sum score that indicates the total amount of enforced changes to less deep sleep due to disturbances in the sleep environment. If several environmental properties have been measured, i.e. if several ambient sensors are used for generating several ambient signals measuring different properties of the environment, for every single property a sub score can be calculated, wherein the respective sub score is indicative of the part of the sum score caused by the respective environmental property.

It is further preferred that the sleep disturbance monitoring apparatus is adapted for being held in a hand of the person or for being worn by the person. The sleep disturbance monitoring apparatus can be implemented, in, for example, a headband, a watch, a cell phone, a personal digital assistant (PDA), an alarm clock, a pillow, a mattress, a mattress top layer, a duvet, pajama, or a night gown. The sleep disturbance monitoring apparatus can therefore preferentially easily be transported from one sleeping site to another sleeping site.

In a further aspect of the present invention a sleep disturbance monitoring method for monitoring a sleep disturbance of a person is presented, wherein the sleep disturbance monitoring method comprises:
 generating an ambient signal over time, the ambient signal being indicative of a property of the environment of the person,
 generating a sleep signal over time, while the person is sleeping, the sleep signal being indicative of the quality of the sleep of the person over time,
 correlating the ambient signal and the sleep signal,
 providing an ambience disturbance profile, the ambience disturbance profile describing which levels and/or changes of an ambient signal are related to disturbed sleep,
 amending the ambience disturbance profile depending on the correlation,
 generating an ambient signal and determining an environmental disturbance factor, which disturbs the sleep, based on a comparison of the generated ambient signal with the ambience disturbance profile, outputting information regarding the determined environmental disturbance factor to the person.

In a further aspect a sleep disturbance monitoring computer program for monitoring a sleep disturbance of a person is presented, wherein the computer program comprises program code means for causing a sleep disturbance monitoring apparatus to carry out the steps of the sleep disturbance monitoring method as described herein, when the computer program is run on a computer controlling the sleep disturbance monitoring apparatus.

It shall be understood that the sleep disturbance monitoring apparatus, the sleep disturbance monitoring method and the sleep disturbance monitoring computer program have similar and/or identical preferred embodiments, as defined in the independent and dependent claims.

It shall be understood that a preferred embodiment of the invention can also be any combination of the dependent claims with the independent claims.

These and other aspects of the invention will be apparent from and elucidated with reference to the embodiments described hereinafter.

DETAILED DESCRIPTION OF EMBODIMENTS

Figure 1:
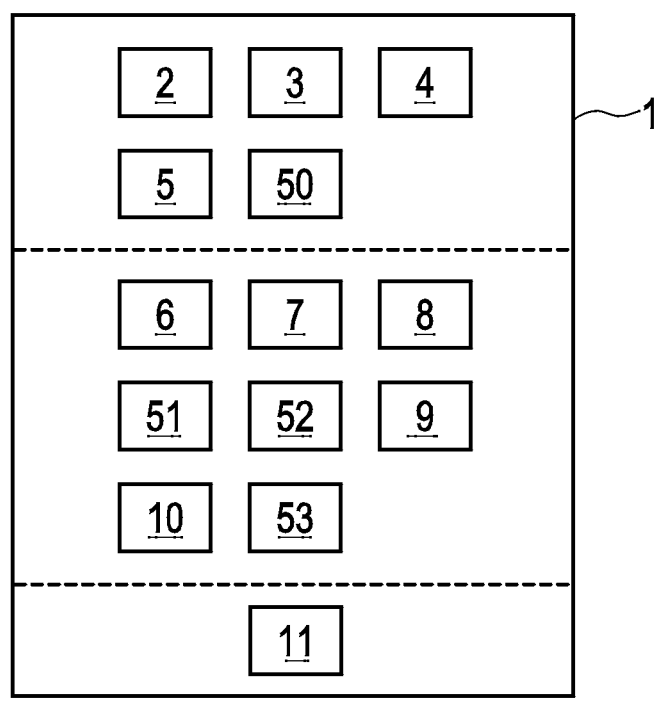
FIG. 1 shows schematically and exemplarily an embodiment of a sleep disturbance monitoring apparatus.

FIG. 1 shows schematically and exemplarily a sleep disturbance monitoring apparatus for monitoring a sleep disturbance of a person. The sleep disturbance monitoring apparatus 1 comprises an ambient sensor 2 for generating an ambient signal over time, while the person is sleeping. The ambient signal is indicative of one or several properties of the environment of the person. The ambient sensor 2 can be an audio sensor such as a microphone; a light sensor such as a white light or color spectrum light intensity sensor; a temperature sensor for measuring ambient temperature and/or skin temperature; an air quality sensor such as an oxygen sensor, a nitrogen sensor, a humidity sensor, a scent sensor; a bed/chair movement sensor, if the person is located on a bed or on a chair, for example, in an aircraft, a bus, a car, a boat or a train. The sleep disturbance monitoring apparatus 1 can comprise one or several of these ambient sensors 2. The ambient signal can be any signal being indicative of properties of the environment of the person including the temperature of the environment directly at the skin of the person, i.e. including the skin temperature.

The sleep disturbance monitoring apparatus 1 further comprises a sleep sensor 3 for generating a sleep signal over time while the person is sleeping. The sleep signal is indicative of the quality of the sleep of the person over time. In this embodiment, the sleep signal represents the sleep depth over time. The sleep signal can be a movement signal which can be determined by using, for example, three-dimensional accelerometry, an infrared camera, and/or sound analysis. The sleep signal can also be an EEG or PSG recording. The sleep signal can also be a signal representing the sleep depth over time, wherein the sleep depth is determined based on, for example, detected movements of the person, EEG or PSG recordings. Also other means can be used to quantify the sleep depth for generating a sleep signal over time.

For example, if the person moves during the sleep, in particular, during consecutive periods, the sleep depth can be determined as being awake or a light sleep stage, whereas, if the person does not move, a deep sleep stage can be determined. For instance, if during a predefined longer time period the person moves within a certain number of consecutive shorter time periods and if this certain number exceeds a predefined threshold, it can be determined that the person is awake or in a light sleep stage, whereas, if the certain number is smaller than the predefined threshold, the person may be in a deep sleep stage. Several threshold can be predefined for distinguishing between different sleep stages. The thresholds can be determined by using calibration measurements, wherein during the calibration measurements the person is in known sleep stages. For determining sleep depth data as sleep signal from movements of the person the software ACTIWARE from Philips Respironics or another known software can be used.

Sleep depth data can be determined depending on EEG recordings by using, for example, known sleep interpretation guidelines defining which characteristics of the EEG recordings corresponds to which sleep depth or sleep stage. For instance, the sleep interpretation guidelines disclosed in "A manual of standardized terminology, techniques and scoring system for sleep stages of human subjects" by Rechtschaffen A. et al., Bethesda: United States Department of Health, Education and Welfare (1968) or disclosed in "The AASM Manual for the Scoring of Sleep and Associated Events: Rules, Terminology and Technical Specifications" by Iber et al., Westchester: American Academy of Sleep Medicine (2007) can be used for determining the sleep stage or the sleep depth depending on the EEG recordings. These articles are herewith incorporated by reference.

The sleep disturbance monitoring apparatus 1 further comprises a correlation unit 4 for correlating the ambient signal and the sleep signal. The correlation unit 4 is adapted to determine whether a change in the ambient signal corresponds to a change in the sleep signal. The correlation unit 4, which can also be regarded as a reasoning engine, can therefore determine whether ambient changes can be seen as an arousal in the sleep signal, in particular, in the sleep depth data.

For correlating the ambient signal and the sleep signal the correlation unit 4 preferentially uses thresholds which can be retrieved from, for example, ambience disturbance profiles which will be described further below. If a change above a threshold in the sleep signal follows shortly within a predefined time period, for example, some seconds or five minutes or less, after a change above a threshold in the ambient signal, it is assumed that the change in the sleep signal is caused by the change in the ambient signal.

The sleep disturbance monitoring apparatus 1 further comprises an ambient disturbance profile providing unit 5 for providing an ambient disturbance profile, wherein the ambient disturbance profile describes which levels and/or changes of the ambient signal are likely to disturb the sleep. The ambience disturbance profile comprises ranges of levels and/or changes of environmental properties, wherein it is likely that the sleep is disturbed, if the level and/or change of the ambient signal is within these ranges. These ranges can be predefined ranges, which are, for example, known from literature published guidelines of the World Health Organization, or, a questionnaire. For instance, if the ambient signal is a noise signal, the continuous noise level should not exceed 30 dB, wherein the non-continuous noise should not exceed 45 dB. Thus, an ambient signal range can be predefined by a continuous noise level being larger than 30 dB and a non-continuous noise being larger than 45 dB. If the ambient sensor 2 measures the room temperature, the ambient signal range can be predefined as including temperatures outside of the temperature range of 18 to 20° C., and if the ambient sensor 2 measures the light intensity, the ambient signal range can be defined as including light intensities larger than 10 lux, because a light intensity being smaller than 10 lux is considered as not disturbing the sleep.

The sleep disturbance monitoring apparatus 1 comprises therefore further an ambience disturbance profile amending unit 50 for amending the ambience disturbance profile depending on the correlation. The ambience disturbance profile amending unit 50 starts preferentially with a provided general ambience disturbance profile which is based on standards found in literature. The ambience disturbance profile will then be adapted in accordance with their correlation between the ambient signal and the sleep signal. In particular, if in accordance with the actual ambience disturbance profile a certain change and/or level of the ambient signal should have caused a change in the sleep signal and if this is actually not the case, the corresponding ranges of the ambience disturbance profile are adapted such that they exclude the actually measured change and/or level of the ambient signal, which has not caused a change in the sleep signal. For instance, if in accordance with the actual ambience disturbance profile a noise level of 30 dB should disturb the sleep and it can be concluded from the correlation that the sleep of the respective person is not disturbed by this noise level the corresponding ranges of the ambience disturbance profile are adapted such that a noise level of 30 dB is outside of these ranges.

The ambience disturbance profile can comprise several ranges related to different environmental factors like temperature, noise, and/or light intensity; and related to possible further characteristics like the time of day, the sleep stage and/or time in bed, wherein the time of day is the actual time like 02:00 or 06:00 and the time in bed is the time that a person spends in bed, either awake or asleep. If, for example, the person falls asleep at 23:00, and it is now 2:00, the time of day is 02:00 and the time in bed is three hours. For example, the ranges can be provided such that it is considered that, if the person is in deep sleep, a certain noise level is less likely to disturb the sleep as compared to light sleep. Thus, the ranges can exclude larger noise levels, if the person is in deep sleep, as compared to light sleep.

By using the correlation between the ambient signal and the sleep signal the ambience disturbance profile amending unit 50 can amend the ambience disturbance profile such that it is personalized. For amending the ambience disturbance profile, the ambience disturbance profile amending unit 50 can use data reasoning techniques such as neural networks.

Preferentially, the sleep signal and the ambient signal used for amending the ambient disturbance profile are measured in habitual settings, i.e. during "regular" nights, in which the person is not affected by, for example, stress, caffeine, food, and/or alcohol. It is also preferred that measurements of the ambient signal and the sleep signal, which have been performed over several nights, are used for amending the ambience disturbance profile.

The sleep disturbance monitoring apparatus 1 further comprises an environmental disturbance determination unit 51 for determining an environmental disturbance factor, which disturbs the sleep, based on a comparison of the generated ambient signal with the ambience disturbance profile. In particular, the environmental disturbance determination unit 51 can be adapted to determine an environmental factor, which is measured by the ambient sensor, as being an environmental disturbance factor, if the level and/or change of the ambient signal is within a range defined by the ambience disturbance profile. For instance, if the ambient signal is a temperature signal and the level of the temperature signal is within a range defined by the ambience disturbance profile, the temperature can be determined as an environmental disturbance factor and this environmental disturbance factor can be output by the output unit.

The environmental disturbance determination unit 51 can further be adapted to classify the environmental disturbance factor into weak, moderate or strong depending on 1) the absolute change or rate of change of the ambient signal and/or 2) the intensity or level of the ambient signal. For example, the ambience disturbance profile can provide change ranges for the absolute change and/or for the rate of change of the ambient signal and level ranges for the level or the intensity of the ambient signal, wherein the change ranges, the level ranges and/or combinations of the change ranges and the level changes can be assigned to a weak class, a moderate class or a strong class. If an ambient signal is within one or several of these ranges, the environmental disturbance factor can be classified in the class, which is assigned to this one or these several ranges.

Information regarding the determined environmental factor is shown on a display 11. Preferentially, the display 11 also shows graphs and/or text to the person, in order to inform the person about the correlation between the ambient signal and the sleep signal.

The sleep disturbance monitoring apparatus further comprises an advice generating unit 52 for generating an advice for improving the sleep quality. The advice generating unit 52 is adapted to generate the advice depending on the determined environmental disturbance factor, wherein the display 11 is adapted to output the advice to the user. The advice generating unit 52 is adapted to generate an advice recommending to increase or decrease the determined environmental disturbance factor such that the sleep can be improved, for example, to increase or decrease the room temperature, to decrease the noise level, and/or to decrease the light intensity.

Figure 2:
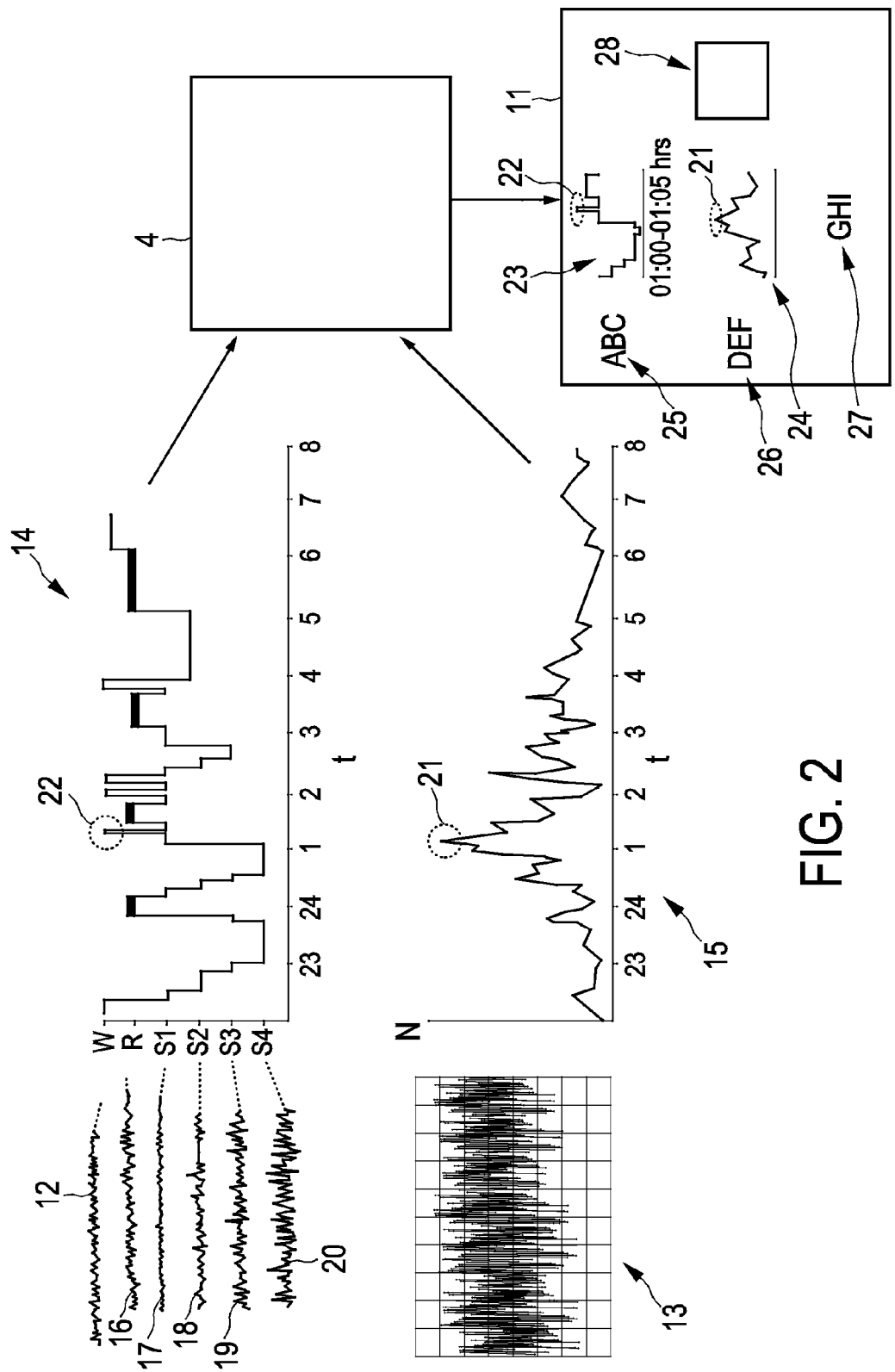
FIG. 2 shows schematically and exemplarily a correlation of an ambient signal and a sleep signal.

FIG. 2 illustrates schematically and exemplarily a correlation between an ambient signal and a sleep signal and how information regarding the correlation can be shown on the display. In this example, the ambient sensor measures EEG recordings which are assigned to certain sleep depth or sleep stages by using the assignments shown in FIG. 2. If an EEG recording is measured, which corresponds to one of the EEG signals 12, 16 to 20 shown in FIG. 2, the respective sleep stage or sleep depth is assigned to the actually measured EEG recording. In particular, if the actually measured EEG recording corresponds to a wake EEG signal 12, a sleep stage or sleep depth is assigned to the actually measured EEG recording, which corresponds to a wake stage of the person. If the EEG recording corresponds to an REM EEG signal 16, a sleep stage or sleep depth is assigned to the actually measured EEG recording, which indicates a REM stage or a REM depth. The further EEG signals 17 to 20 are assigned to sleep stages or sleep depths S1 to S4. The actually measured EEG recording leads to one of the sleep stages or sleep depths S1 to S4, which correspond to the EEG signals 17 to 20, respectively, by comparing the EEG signals 17 to 20 with the actually measured EEG recording. Moreover, the sleep stages or sleep depths can be determined based on measured EEG recordings using the strict sleep interpretation guidelines disclosed in the above mentioned articles by Rechtschaffen et al. and Iber et al.

The assignment between the EEG signals 12, 16 to 20 and certain sleep stages or sleep depths can be determined by, for example, calibration measurements, wherein the actually present sleep stage or sleep depth is known from another means for measuring the sleep stage or sleep depth like a movement detector. By using these assignments, the sleep signal 14 can be generated, which shows the sleep depth over time t, wherein W indicates a wake stage, R an REM stage and S1 to S4 indicate further stages which correspond to larger sleep depths.

In this example, the ambient sensor comprises a microphone for generating a microphone signal 13 and extracts the noise level 15, wherein the noise level 15 is regarded as being the ambient signal in this example. The noise level 15 is determined by using a filtering unit, which is adapted to filter the microphone signal 13 such that the noise level 15 substantially contains only ambient noise, and not noise of the person like breathing noise or snoring noise. The filtering unit is preferentially a frequency filter, wherein the frequencies, which are allowed to pass the filtering unit, can be determined by calibration measurements, wherein the microphone signal is measured while known noise sources are present.

The sleep signal 14 and the ambient signal 15 are provided to the correlation unit 4 for correlating the ambient signal 15 and the sleep signal 14. In this example, the correlation unit 4 determines that the peak 21 of the ambient signal 15 caused the wake stage 22 of the sleep signal 14, because the level of the peak 21 is within a corresponding noise range defined by the ambient disturbance profile and because the change in the sleep signal is above a corresponding predefined threshold, wherein the wake stage 22 follows the peak 21 and wherein the temporal difference between the wake stage 22 and the peak 21 is smaller than a predefined time period. Adequate time periods can be determined by previous measurements, in particular, by calibration.

In this example, the display 11 shows a sleep cutout 23 of the sleep signal 14 and an ambient cutout 24 of the ambient signal 15 for illustrating the correlation between the peak 21 and the peak 22. A first text 25 indicates that the upper sleep cutout 23 relates to the sleep signal and a second text 26 indicates that the lower ambient cutout 24 relates to the ambient signal 15 which is, in this example, a noise level signal. A third text 27 can be shown on the display 11, which further explains the correlation. In this example, it is explained at which time and in which sleep depth the sleep was disturbed by noise. The display further shows a playback button 28, wherein if the playback button 28 is pushed, the development of the sleep signal 14 and the ambient signal 15 over time, while the person were sleeping, is shown on the display 11. The display 11 can be regarded as a graphical user interface, wherein a user can push the playback button 28, for example, by using a mouse or by touching the screen, if the display comprises a touch screen. Instead of providing the playback button on the display 11, the playback button can also be provided on another part of the sleep disturbance monitoring apparatus.

The sleep disturbance monitoring apparatus 1 further comprises a sleep signal calculation unit 6 which determines the calculated sleep signal over time from the ambient disturbance profile and the generated ambient signal, without using the sleep sensor 3 for generating the sleep signal. Thus, for example, in a training phase the sleep sensor 3 and the ambient sensor 2 are used for generating a sleep signal, in this embodiment, sleep depth data, and an ambient signal for amending the ambient disturbance profile. After the training phase and after the ambient distance profile has been amended, the calculated sleep signal over time, which is indicative of the quality of the sleep of the person over time, is calculated from the ambient disturbance profile and the ambient signal, which is generated during the actual sleep of the person. A sleep signal over time being indicative of the quality of the sleep of the person can therefore be calculated, without actually measuring a sleep signal while the person is sleeping.

The ambient sensor 2 can be adapted to generate an actual ambient signal being indicative of properties of the environment before the person sleeps, wherein the sleep disturbance monitoring apparatus further comprises an expected sleep quality determination unit 7 for determining an expected sleep quality from the actual ambient signal, which is indicative of properties of the environment before the person sleeps, and from the ambient disturbance profile. The expected sleep quality determination unit 7 allows to give a prognosis on expected sleep quality by sampling the properties of the environment like the noise, light, and temperature characteristics just before going to sleep by using the one or several ambient sensors 2 and by determining the expected sleep quality from the actually measured one or several ambient signals and the ambient disturbance profile.

Instead of using only the ambient signal measured immediately before the person sleeps, also ambient signals can be used, which have been measured during previous habitual sleeping times, in particular, during previous nights. The expected sleep quality can, for example, be calculated as the ratio of the time being expected to be disturbed during the sleep to the total sleep time, wherein the time, during which a disturbance of sleep is expected, can be determined by comparing the ambience disturbance profile with the ambient signal. For example, if several ambient sensors measure several ambient signals related to different environmental properties like temperature, noise, and/or light intensity and if the level and/or change of the ambient signals is not within the ranges defined by the ambient disturbance profile, the expected sleep quality can be determined as being a good sleep quality.

The sleep disturbance monitoring apparatus 1 further comprises a disturbed period determination unit 8 for determining a disturbed period during which the environment potentially disturbed the sleep. The disturbed period determination unit 8 is adapted to determine the disturbed period depending on the ambient signal and a predefined ambient signal range, wherein if the ambient signal is within the ambient signal range, it is assumed that the environment disturbs the sleep. The ambient signal range is preferentially retrieved from the ambience disturbance profile. The sleep disturbance monitoring apparatus 1 can, for example, count or sum the events or time spent in an environmental situation that is considered as not being optimal for sleeping. The disturbed period determination unit 8 can be adapted to determine several disturbed periods, during which the person is disturbed while sleeping. The sum of these disturbed periods can be related to the total sleep time for determining a sum score that indicates the total amount of sleep disturbance in the sleep environment. For example, this sum score can be provided as the ratio of the sum of the disturbed periods to the complete sleeping time in percent. If several properties of the environment have been measured by using several ambient sensors 2, for example, if the noise, the temperature, the light intensity and/or the humidity have been measured as the several properties, for each single property a sub score can be calculated, wherein the sub score indicates the part of the sum of the disturbed periods or of the complete sleeping time, which has been disturbed by the respective property.

The sleep disturbance monitoring apparatus further comprises a sleep depth transition determination unit 9 for determining sleep depth changes from a larger sleep depth, i.e. a deeper sleep, to a lighter sleep depth, i.e. a shallower sleep, based on the sleep signal, and a sleep transition period determination unit 10 for determining a sleep transition period during which the sleep depth changes from a larger sleep depth to a lighter sleep depth based on the determined sleep depth changes. If the sleep signal does not already directly represent the sleep depth, the sleep depth transition determination unit determines the sleep depth from the sleep signal and determines than sleep depth changes from a larger sleep depth to a lighter sleep depth based on the sleep depth determined from the sleep signal. The sleep disturbance monitoring apparatus further comprises a disturbed sleep period determination unit 53 for determining a disturbed sleep period depending on the determined sleep transition period and the ambient signal. A disturbed sleep period defines a period during which the sleep was disturbed by an environmental disturbance factor like noise, and/or temperature. The disturbed sleep period determination unit 53 can be adapted to count or sum the events or times spend in an environmental situation within the time frame determined by the sleep transition period determination unit 10. In particular, the disturbed sleep period determination unit 53 can be adapted to count or sum the events or times spent in an environmental situation that coincides with sleep changes towards a lighter sleep depth. The sleep transition periods are correlated with the ambient signal, in order to determine which sleep transition period coincides with which change in the properties of the environment. For example, if during a sleep transition period, during which the sleep depth changes from a deeper sleep to a shallower sleep, noise above a predefined threshold has been determined as environmental disturbance factor, this sleep transition period can be determined as being a disturbed sleep period which is caused by noise. In particular, it can be determined whether recorded noise coincides with a shift to lighter sleep or even wake. The sleep transition periods can therefore be classified in accordance with correlated changes in the ambient signal, i.e. in the properties of the environment, in order to determine disturbed sleep periods. During a sleep of the person, several disturbed sleep periods can be determined which are related to one or several properties of the environment. The sum of these disturbed sleep periods can be regarded as a sum score that indicates the total amount of enforced changes to less deep sleep due to disturbances in the sleep environment. The sum score can be provided as a ratio of the sum of the disturbed sleep periods to the overall sleep time, in particular, in percent. If several environmental properties have been measured, i.e. if several ambient sensors are used for generating several ambient signals being indicative of different properties of the environment, for every single property a sub score can be calculated, wherein the respective sub score is indicative of the part of the sum score caused by the respective environmental property.

Figure 3:
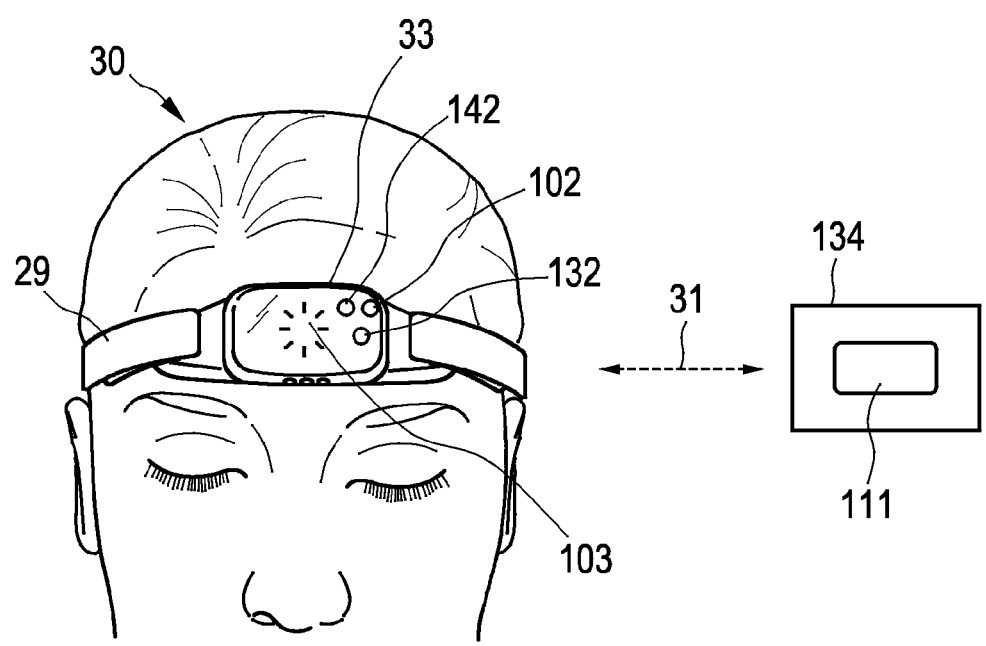
FIG. 3 shows schematically and exemplarily a headband comprising parts of the sleep disturbance monitoring apparatus.

The sleep disturbance monitoring apparatus 1 is adapted for being portable. For example, the sleep disturbance monitoring apparatus 1 can be adapted to be held in a hand of the person or for being worn by the person in different places on the body, one example being the wrist. FIG. 3 shows an embodiment of the sleep disturbance monitoring apparatus comprising a headband 29 to be worn by a person 30. The headband 29 comprises a casing 33 including a sleep sensor 103 and ambient sensors 102, 132, 142. In this embodiment, the sleep sensor 103 comprises an EEG sensor and the ambient sensors 102, 132, 142 comprise a microphone, a light sensor and a temperature sensor, respectively. The display and the further units are provided in a separate unit 134, wherein in FIG. 3 only the display 111 is shown. The unit 134 comprising the display 111 and the further units is wirelessly connected to the sleep sensor 103 and the ambient sensors 102, 132, 142 via a data connection 31, in order to transmit the ambient signal and the sleep signal to the further units. In another embodiment, the display and/or the further units can also be located within the headband 29, in particular, within the casing 33.

Figure 4:
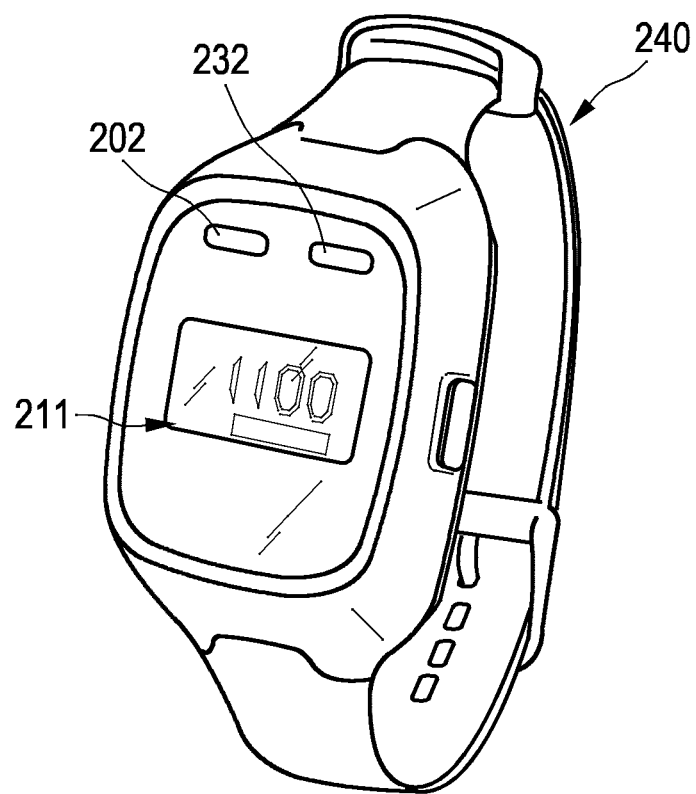
FIG. 4 shows schematically and exemplarily a realization of the sleep disturbance monitoring apparatus as a watch.

FIG. 4 shows a further embodiment of the sleep disturbance monitoring apparatus. In this embodiment, the different units and sensors of the sleep disturbance monitoring apparatus are integrated into a watch 240. The watch 240 comprises, in particular, ambient sensors 202, 232 and a sleep sensor, which is, in this embodiment, located within the watch 240. The ambient sensor 202 comprises, for example, a microphone, and the ambient sensor 232 comprises, for example, a spectrum light sensor. The sleep sensor can comprise a motion sensor, wherein the motion signal can be regarded as a sleep signal or the motion signal is translated into sleep depth data forming the sleep signal. A display 211 is adapted to show a person information regarding, for example, the correlation of the ambient signals and the sleep signal.

Figure 5:
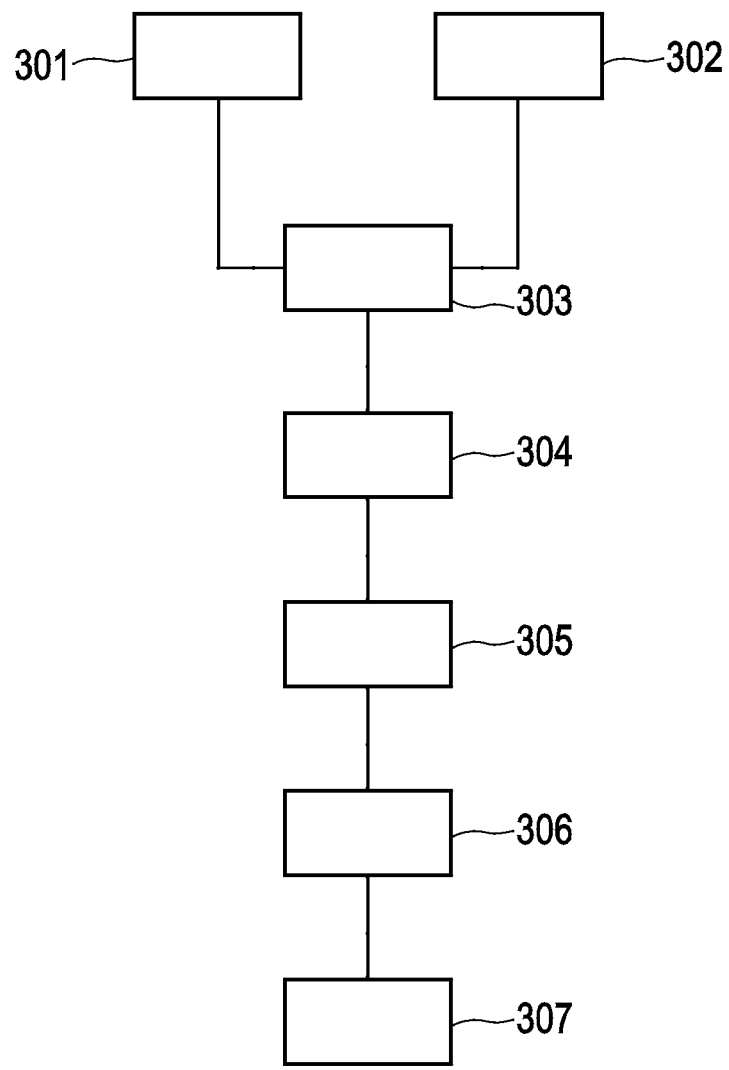
FIG. 5 shows a flowchart exemplarily illustrating an embodiment of a sleep disturbance monitoring method.

In the following an embodiment of a sleep disturbance monitoring method for monitoring a sleep of a person will exemplarily be described with reference to a flowchart shown in FIG. 5. In step 301, an ambient signal is generated over time while the person is sleeping, wherein the ambient signal is indicative of a property of the environment of the person. For example, a noise level can be measured over time as an ambient signal or another property of the environment of the person can be measured. In step 302, a sleep signal is generated over time, while the person is sleeping, wherein the sleep signal is indicative of the quality of the sleep of the person over time. For example, a sleep depth can be determined over time based on, for example, EEG recordings and/or a movement detection signal, as the sleep signal. Steps 301 and 302 are performed simultaneously, while the person is sleeping. In step 303, the ambient signal and the sleep signal are correlated, and, in step 304, an ambience disturbance profile is provided, wherein the ambient disturbance profile describes which levels and/or changes of the ambient signal are related to disturbed sleep. In step 305, the ambience disturbance profile is amended depending on the correlation. In step 306, an ambient signal is generated while the person is currently sleeping and an environmental disturbance factor, which disturbs the sleep, is determined based on a comparison of the generated ambience signal with the ambience disturbance profile. In step 307, information regarding the environmental disturbance factor is output to the person.

Steps 301 to 305 are preferentially performed in a training phase, in which the ambience disturbance profile is personalized depending on the correlation. Step 306 is then preferentially performed during an actual sleep by using the personalized ambience disturbance profile, which has been amended in the training phase. Once the ambience disturbance profile has been amended in the training phase, the amended ambience disturbance profile can be used during several nights, while steps 306 and 307 are performed, without amending the ambience disturbance profile again. The training phase, i.e. steps 301 to 305, can be performed, for example, in regular time intervals or if the sleeping environment has changed, for instance, because the person has changed the sleeping room.

Known sleep coaching devices give consumers insight in how long and well they have slept, and provide advice on how to improve their sleep quality. One of the features is to help them to analyze how disturbances during the night have impacted their sleep quality, by using questionnaires on disturbances that they have noticed and relating this back to EEG-based sleep quality.

Environmental disturbances such as noise, light, humidity and temperature variations can have a negative impact on sleep quality. This is obvious if a person is consciously woken by such disturbances. However, also disturbances that do not result in conscious wake up can have a strong impact on a persons sleep quality. This impact affects people's mood, memory, performance, well-being and quality of life in a negative way.

People sleeping in a house that is close to a high way, railway or airport are facing a disturbed sleep. For example, noise can lead to suppression of the 'slow waves' that are characteristic for deep sleep. Because of the brain waves, important information is stored and less important information is released to make room for new information. Even a mild sleep disruption that suppresses slow-wave activity and induces shallow sleep, but does not reduce total sleep time, can be sufficient to affect subsequent successful encoding-related hippocampal activation and memory performance in healthy human subjects. Thus, even a light disruption of deep sleep without a person waking up can affect memory and learning capacity negatively.

Light intrusion, even if dim, is likely to have measurable effects on sleep disruption and melatonin suppression. Even if these effects are relatively small from night to night, continuous chronic circadian, sleep and hormonal disruption may have longer-term health risks.

Ambient temperature can be an important determinant of sleep quality since thermoregulation affects the mechanism regulating sleep. In humans, cold exposure during sleep can increase wakefulness and can decrease REM sleep and light sleep. Moreover, induction of a small increase in skin temperature, whilst not altering core temperature, can suppress nocturnal wakefulness and can shift sleep to deeper stages in young and, especially, in elderly healthy and insomniac participants. Elderly subjects show such a pronounced sensitivity that it almost doubled the proportion of nocturnal slow wave sleep and decrease the probability of early morning awakening from 0.58 to 0.04.

Noise, light, humidity and temperature may have negative effects on people's sleep and as a consequence on various vital human functions such as mood, memory, performance, well-being and quality of life in general, even up to damaging long-term effects that may contribute to cardiovascular disease, Alzhiemer's disease and even cancer.

If people know about nightly disturbances that unconsciously impact their sleep quality, they would be able to take adequate countermeasures. If the source is being identified as being in-house, they can remove or modify the source. If the source is being identified as being out-house, they can take countermeasures such as earplugs, eye masks, socks, improving noise, light and temperature isolation in the bedroom, for example, by using doubled glassed windows and/or thicker curtains, silent airconditioning, talk to house-mates to be more considerate with noise and light, and so on. This may be especially relevant for people that sleep in varying or difficult environments, such as travelers, tourists, airway personnel, truck drivers, and shift-workers, because they have to protect themselves against daytime disturbances.

The sleep disturbance monitoring apparatus 1 can measure one or more environmental parameters such as noise, light, humidity, temperature, and other parameters and can relate this to sleep quality. The correlations between these measurements, for example, when environmental noise might have resulted in lower sleep quality or lower sleep depth, can be presented to the user.

The sleep disturbance monitoring apparatus 1 can be adapted to record, quantify and characterize noise, light, humidity and/or temperature changes throughout the night, by means of a microphone, lux meter, thermistor, humidity sensor, and/or other sensors. Besides that, the sleep disturbance monitoring apparatus can be adapted to simultaneously record the sleep depth (light or deep sleep) by means of a sleep sensor, which may also be regarded as a sleep screener. The sleep sensor detects the sleep depth of a sleeping person using certain physiological measurements. Deep sleep can be detected by means of EEG or movement analysis (for example, using actigraphs, camera, sound analysis). The sleep disturbance monitoring apparatus can be adapted to relate the measured noise, light, and/or temperature to the measurements of the sleep sensor, and analyse when environment changes had a negative effect on the sleep quality.

The sleep disturbance monitoring apparatus 1 can be adapted to display the (absolute, average and range) ambient noise, light, and/or temperature levels that were present in the bedroom throughout the night, and to show or play back recorded disturbances that were classified as being disturbing for your sleep quality or sleep depth. Moreover, the sleep disturbance monitoring apparatus can be adapted to give an indication of how much the environment change disturbed the sleep quality or sleep depth and point out direct links between environmental changes and sleep changes. This information is presented to the user via the display such that the user can take counter measures to prevent these kinds of disturbances in the future. The sleep disturbance monitoring apparatus can be adapted to give advice on how to take these countermeasures. This can also be interesting for insomnia patients to find the factors that might interfere with their sleep, and also for their sleep specialists or cognitive behavioral therapists, to get more insight into the patient's situation at home and adapt diagnosis, treatment, and sleep hygiene advice that is tailored to this information.

The sleep disturbance monitoring apparatus can be adapted to use reasoning techniques such as neural networks to create a unique ambience disturbance profile, i.e., for example, individual quantification of bandwidth and peak level of sleep disturbing changes in noise, light, temperature, and/or humidity, as well as other environmental factors. Over time, the sleep disturbance monitoring apparatus will then learn what type and level of disturbances always influence the sleep depth negatively; independent of the sleep depth the person is in. When the sleep disturbance monitoring apparatus has learned this and built a profile, then it can simply track if disturbances of this type and level were measured during the night, without needing to measure the actual sleep depth disturbances, because it has learned that with this kind of ambient disturbances the sleep depth will be disturbed. The sleep disturbance monitoring apparatus is preferentially also adapted to give a prognosis on expected sleep quality, by sampling the noise, light, and temperature characteristics just before going to sleep, and possibly give a warning when poor sleep quality is to be expected.

The sleep disturbance monitoring apparatus may be used as an environment disturbance awareness system for sleep enhancement for home environments. The system could be implemented in or attached to bedroom-products such as an alarm clock or the wake-up light by Philips. This system would give people insight into how much their sleep is disturbed by noises inside or outside their home, partners arriving later in bed or getting up early that are using too much light, or when the temperature changes in the room are too disturbing, for example, because the window is opened too far during the night.

The sleep disturbance monitoring apparatus may also be used as an environment disturbance awareness system for sleep enhancement for hotel and other hospitality environments like outdoor camping. A frequent problem is sleep disturbance because of noise in an unfamiliar environment. Information on the noise disturbance level of a hotel room could be linked to a user's own unique noise disturbance profile, i.e., for example, individual quantification of bandwidth and peak level of sleep disturbing noises, and hence advice the user, who may be a hotel guest, on expected sleep quality. The same can be done for light, temperature, and other environmental parameters. This will enable the user to take countermeasures before actually going to sleep. The expected sleep advice could also be implemented in the home system discussed above.

The sleep disturbance monitoring apparatus may also be used as an environment disturbance awareness system for sleep enhancement for travel environments. Sleeping in an airplane, train, bus, car or boat can result in various disturbances, which can vary a lot due to different weather circumstances. The environment disturbance awareness system could then help travel personnel in taking countermeasures, when they see that the sleep quality of their travelers is degrading due to disturbances. As such two types of systems may be provided for these environments. A first type can be a personal environment disturbance awareness system, that gives the individual feedback of how his sleep was disturbed by the environment during the journey. But also this system can give a prognosis on how well the user will likely sleep, and can give advice on how to improve it. For example, it could advice to put on extra clothes if the system notices that the user will likely get a little too cold later on when he is asleep. A second type can be a networked system in which multiple travelers wear environment disturbance awareness devices, of which the information is sent to a central unit for the travel personnel to react to when they see that their passenger's sleep is degrading. They can then try to block sound or light for certain passengers, or carefully put on or take off blankets in an effort to give the individual passengers the best sleep possible.

The sleep disturbance monitoring apparatus may also be used as an environment disturbance awareness system for healthcare, i.e., for example, insomnia patients can show their own recordings and data to their cognitive behavioral therapists, which will give them more insight into the factors that may impede the insomnia patient's sleep, and hence can be used for diagnosis, treatment and advice on sleep hygiene issues.

Although in the above described embodiments certain ambient sensors have been used for generating an ambient signal over time, while the person is sleeping, in other embodiments also other ambient sensors can be used for generating an ambient signal being indicative of a property of the environment of the person. Moreover, although in the above described embodiments certain sleep sensors have been described, in other embodiments also other sleep sensors can be used for generating a sleep signal over time, which is indicative of the quality of the sleep of the person over time.

Although in the embodiment described above with reference to FIG. 3 parts of the sleep disturbance monitoring apparatus are located in a headband and although in the embodiments described above with reference to FIG. 4 the sleep disturbance monitoring apparatus is integrated into a watch, the sleep disturbance monitoring apparatus can also be incorporated in other objects, inter alia, in an alarm clock, a cell phone, or a PDA.

The information regarding the determined environmental factor can be displayed to the person in different ways. For example, for different environmental factors traffic lights can be shown, wherein if the respective environmental factor did not disturb the sleep, a green light is shown, if the respective environmental factor is likely to have disturbed the sleep, a yellow light is shown, and if the respective environmental factor has truly disturbed the sleep, a red light is shown.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations, determinations, and/or correlations, performed by one or several units or devices can be performed by any other number of units or devices. For example, the correlation of the ambient signal and the sleep signal, the amendment of the ambience disturbance profile, the provision of the calculated sleep signal over time, the determination of the expected sleep quality, the determination of the disturbed period during which the environment potentially disturbs the sleep, the determination of the sleep depth changes from a larger sleep depth to a lighter sleep depth, the determination of the sleep transition period, the determination of the environmental disturbance factors, can be performed by a single unit or by any other number of different units. The calculations, determinations, correlations and/or the control of the sleep disturbance monitoring apparatus in accordance with the sleep disturbance monitoring method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems. In the case where the computer program is distributed via the Internet, all of the collected data (e.g., from the environmental disturbance factors), additional calculations, determinations, correlations, is uploaded to a web service or website where this website acts as the advice generating unit and generates advice for improving sleep quality. Software updates and/or control of the sleep disturbance monitoring apparatus in accordance with the sleep disturbance monitoring method could also be performed by communication via the Internet and this website.

Any reference signs in the claims should not be construed as limiting the scope.

The invention relates to a sleep disturbance monitoring apparatus for monitoring a sleep disturbance of a person. An ambience disturbance profile, which describes which levels and/or changes of an ambient signal, which is, for example, a temperature signal or a noise signal, are related to disturbed sleep, is amended depending on a correlation between the ambience signal and a sleep signal which is indicative of the quality of the sleep of the person. After the ambience disturbance profit has been amended, an environmental disturbance factor, which disturbs the sleep, is determined based on a comparison of an actual ambient signal with the amended ambience disturbance profile, wherein information regarding the determined environmental disturbance factor is output to the person on an output unit. This allows providing personalized information regarding environmental sleep disturbance factors, i.e. the information considers the individual susceptibility of a person for environmental disturbances during sleep.

The invention claimed is:

1. A sleep disturbance monitoring apparatus for monitoring a sleep disturbance of a person, the sleep disturbance monitoring apparatus comprising:
    a sensor configured to generate an ambient signal, the ambient signal being indicative of a property of the environment of the person,
    an ambience disturbance profile providing unit, comprising a plurality of personalized settings associated with different sleep state conditions of the person, configured to:
        provide an ambience disturbance profile describing which of at least: levels and changes of an ambient signal are related to a disturbed sleep of a current sleep state condition,
    a second sensor configured to generate a sleep signal over time, while the person is sleeping, the sleep signal being indicative of a quality of the sleep of the person over time,
    a correlation unit configured to:
        correlate the ambient signal and the sleep signal to determine whether a change in the ambient signal corresponds to a change in the sleep signal,
    an environmental disturbance determination unit-configured to determine an environmental disturbance factor causing an arousal correlation between changes in the ambient signal and the sleep signal, wherein the environmental disturbance factor is based on a comparison of a generated ambient signal with the ambience disturbance profile,
    an ambience disturbance profile amending unit configured to amend the personalized setting of the current sleep state in ambience disturbance profile based on the correlation indicating the arousal correlation between changes in the ambient signal and the sleep signal, wherein the determined environmental disturbance factor within the personalized ambience disturbance profile is amended depended on the change in the sleep signal, and
    an output unit-configured to output information regarding the determined environmental disturbance factor to the person.

2. The sleep disturbance monitoring apparatus as defined in claim 1, wherein the sleep disturbance monitoring apparatus further comprises:
    an advice generating unit configured to generate an advice for improving the sleep quality based on the determined environmental disturbance factor, and wherein the output unit is configured to output the advice to the user.

3. The sleep disturbance monitoring apparatus as defined in claim 1, wherein the sleep disturbance monitoring apparatus further comprises a sleep signal calculation unit configured to provide a calculated sleep signal over time from the ambience disturbance profile and the ambient signal.

4. The sleep disturbance monitoring apparatus as defined in claim 1, wherein the sleep disturbance monitoring apparatus further comprises:
    an expected sleep quality determination unit configured to determine an expected sleep quality from the ambient signal and the ambience disturbance profile.

5. The sleep disturbance monitoring apparatus as defined in claim 3, wherein the sleep disturbance monitoring apparatus further comprises:
    a disturbed period determination unit configured to determine a disturbed period during which the environment potentially disturbed the sleep, depending on the ambient signal and the ambience disturbance profile.

6. The sleep disturbance monitoring apparatus as defined in claim 1, wherein the sleep disturbance monitoring apparatus comprises:
    a sleep depth transition determination unit configured to determine sleep depth transitions over time based on the sleep signal,
    a sleep transition period determination unit configured to determine a sleep transition period during which the sleep depth changes over time based on the determined sleep depth transitions,
    a disturbed sleep period determination unit configured to determine a disturbed sleep period depending on the determined sleep transition period and the ambient signal.

7. The sleep disturbance monitoring apparatus as defined in claim 1, wherein the sleep disturbance monitoring apparatus is adapted for one of: being held in a hand of the person and for being worn by the person.

8. The sleep disturbance monitoring apparatus as defined in claim 7, wherein the sleep disturbance monitoring apparatus is adapted for being worn by the person as a watch.

9. A sleep disturbance monitoring method for monitoring a sleep disturbance of a person, the sleep disturbance monitoring method comprising:
    in a sleep disturbance monitoring apparatus:
        generating by a sensor, an ambient signal over time, the ambient signal being indicative of a property of the environment of the person,
        generating by a quality of sleep unit, a sleep signal over time, while the person is sleeping, the sleep signal being indicative of a quality of the sleep of the person over time,
        providing, by an ambience disturbance profile determining unit, an ambience disturbance profile comprising a plurality of personalized settings associated with different sleep state conditions of the person, the ambience disturbance profile describing which of at least: levels and changes of an ambient signal are related to a disturbed sleep of a current sleep state condition, correlating, by a correlation unit, the ambient signal and the sleep signal, determining an environmental disturbance factor, causing an arousal correlation between changes in the ambient signal and changes in the sleep signal, wherein said environmental disturbance factor is based on a comparison of the ambient signal with the ambience disturbance profile, an ambience disturbance profile amending unit-configured to amend the personalized setting of the current sleep state in the ambience disturbance profile based on the correlation indicating the arousal correlation between changes in the ambient signal and the sleep signal, wherein the determined environmental disturbance factor within the personalized ambience disturbance profile is amended depended on the change in the sleep signal, and outputting information regarding the determined environmental disturbance factor to the person.

10. A sleep disturbance monitoring computer program for monitoring a sleep disturbance of a person, the computer program comprising program code for causing a sleep disturbance monitoring apparatus to carry out the steps of a sleep disturbance monitoring method, when the computer program is run on a computer controlling the sleep disturbance monitoring apparatus, wherein the sleep disturbance monitoring method comprises:

generating an ambient signal over time, the ambient signal being indicative of a property of the environment of the person, generating a sleep signal over time, while the person is sleeping, the sleep signal being indicative of a quality of the sleep of the person over time, providing an ambience disturbance profile comprising a plurality of personalized settings associated with different sleep state conditions of the person, the ambience disturbance profile describing which of at least: levels and changes of an ambient signal are related to a disturbed sleep of a current sleep state condition, correlating the ambient signal and the sleep signal, determining an environmental disturbance factor causing an arousal correlation between changes in the ambient signal and changes in the sleep signal, said environmental disturbance factor being based on a comparison of the generated ambient signal with the ambience disturbance profile, an ambience disturbance profile amending unit-configured to amend the personalized setting of the current sleep state in the ambience disturbance profile based on the correlation indicating the arousal correlation between changes in the ambient signal and the sleep signal, wherein the determined environmental disturbance factor within the personalized ambience disturbance profile is amended according to the personalized sleep state conditions depended on the change in the sleep signal, and outputting information regarding the determined environmental disturbance factor to the person.

11. A computer-readable storage-medium that is not a transitory propagating signal or wave, the medium comprising control information for a method of operating a sleep disturbance monitoring apparatus for monitoring a sleep disturbance of a person, the sleep disturbance monitoring method comprising:

in a sleep disturbance monitoring apparatus:

generating by a sensor, an ambient signal over time, the ambient signal being indicative of a property of the environment of the person, generating by a quality of sleep unit, a sleep signal over time, while the person is sleeping, the sleep signal being indicative of a quality of the sleep of the person over time, providing, by an ambience disturbance profile determining unit, an ambience disturbance profile comprising a plurality of pesonalized settings associated with different sleep state conditions of the person, the ambience disturbance profile describing which of at least: levels and changes of an ambient signal are related to a disturbed sleep of a current sleep state condition, correlating by a correlation unit, the ambient signal and the sleep signal;

determining, by an environmental disturbance determination unit, an environmental disturbance factor causing indicating an arousal correlation between changes in the ambient signal and changes in the sleep signal the environmental disturbance factor being based on a comparison of the ambient signal with the ambience disturbance profile, an ambience disturbance profile amending unit-configured to amend the personalized setting of the current sleep state in the ambience disturbance profile based on the correlation indicating the arousal correlation between changes in the ambient signal and the sleep signal, wherein the determined environmental disturbance factor within the personalized ambience disturbance profile is amended depended on the change in the sleep signal, and outputting information regarding the determined environmental disturbance factor to the person.

* * * * *